United States Patent
Tateno et al.

(10) Patent No.: US 6,818,026 B2
(45) Date of Patent: Nov. 16, 2004

(54) PROCESS FOR PRODUCING FATTY ACID ESTERS AND FUELS COMPRISING FATTY ACID ESTER

(75) Inventors: Tatsuo Tateno, Niihama (JP); Toshio Sasaki, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/783,031

(22) Filed: Feb. 15, 2001

(65) Prior Publication Data

US 2001/0042340 A1 Nov. 22, 2001

(30) Foreign Application Priority Data

Feb. 17, 2000 (JP) ........................................ 2000-039316
Feb. 17, 2000 (JP) ........................................ 2000-039318

(51) Int. Cl.⁷ ................................................ C10L 1/18
(52) U.S. Cl. ...................... 44/385; 508/463; 554/167; 554/174
(58) Field of Search ............................. 44/385; 554/167, 554/174; 508/463

(56) References Cited

U.S. PATENT DOCUMENTS

| | | | |
|---|---|---|---|
| 4,161,483 A | * 7/1979 | Cahen | ........................ 554/144 |
| 5,713,965 A | 2/1998 | Foglia et al. | |
| 5,734,070 A | * 3/1998 | Tacke et al. | ................. 554/144 |
| 5,908,946 A | 6/1999 | Stern et al. | |
| 6,090,959 A | * 7/2000 | Hirano et al. | ................ 554/169 |
| 6,187,939 B1 | * 2/2001 | Sasaki et al. | ................ 554/169 |

FOREIGN PATENT DOCUMENTS

| | | |
|---|---|---|
| ES | 2124166 | 1/1999 |
| GB | 795573 | * 5/1958 |
| JP | 61254255 | 11/1986 |
| JP | 7197047 | 8/1995 |
| JP | 9235573 | 9/1997 |
| JP | 200044984 | 2/2000 |
| WO | WO 9601304 | 1/1996 |
| WO | WO 0005327 | 2/2000 |
| WO | WO0005327 | 2/2000 |

OTHER PUBLICATIONS

Ullmann's Enclyclopedia of Industrial Chemistry, Fifth Completely Revised Edition, vol. A10 (1987), p. 281.
Ullmann's Encyclopedia of Industrial Chemistry, Fifth Completely Revised Edition, vol. 11 (1976), p. 432.
Udo R. Kreutzer, Journal of the American Oil Chemists' Society, vol. 61, No. 2.
G.R. Peterson et al.; Journal of the American Oil Chemists' Society, vol. 61, No. 10, 1984, pp. 1593–1597.
Shiro Saka et al.; Biomass, Proc. Biomass Conf. Am., vol. 1, 1999, pp. 797–801.

* cited by examiner

*Primary Examiner*—Cephia D. Toomer
(74) *Attorney, Agent, or Firm*—Birch, Stewart, Kolasch & Birch, LLP

(57) ABSTRACT

A process for producing a fatty acid ester with a high yield from an oil or fat and an alcohol which comprises reacting an oil or fat with an alcohol in the presence of a solid base catalyst under conditions in which at least one of the oil or fat and the alcohol is in a supercritical state at a temperature exceeding 260° C.

11 Claims, No Drawings

PROCESS FOR PRODUCING FATTY ACID ESTERS AND FUELS COMPRISING FATTY ACID ESTER

BACKGROUND OF THE INVENTION

1. Field of the Invention

The present invention relates to a process for producing a fatty acid ester and glycerol by reacting an oil or fat with an alcohol, and to a fuel comprising a fatty acid ester obtained by the above process.

2. Description of Related Art

A principal component of the oil or fat is esters composed of a fatty acid and glycerol, called triglycerides. Fatty acid esters obtained by transesterification of an oil or fat with an alcohol have found wide applications as industrial raw materials, pharmaceuticals and so on.

Processes have been described for manufacturing fuels for diesel engine or base oils for lubricant oil containing fatty acid esters as substitutes for the conventional mineral oils, by transesterification of an oil or fat with an alcohol. For example, in JP-A-9-235573 and JP-A-7-197047, a fuel for diesel engine is produced by reacting a waste edible oil and methanol in the presence of sodium hydroxide. In JP-A-7-197047, transesterification is usually carried out with an alkali catalyst such as sodium hydroxide under the atmospheric pressure at a temperature of 50 to 70° C. In this case, a pre-treatment is essential because, when a free fatty acid exists in an oil or fat as a raw material, it reacts with the alkali catalyst to form a soap. In addition, a after-treatment for separation is also required because a small amount of a soap is produced in the course of the transesterification even when the pre-treatment is carried out.

On the other hand, it has been known that, when the transesterification is carried out under conditions of 9 to 10 MPa and 220 to 250° C., an oil or fat of a low purity containing free fatty acids can be used as a raw material [Ullmann's Encyclopedia of Industrial Chemistry, Fifth Completely Revised Edition, Vol. A10 (1987), p. 281].

In addition, in U.S. Pat. No. 5,713,965, a technology is disclosed in which a fuel for diesel engine and a lubricant oil containing fatty acid esters are produced from an oil or fat and an alcohol in the presence of a lipase in a hexane solvent. An example has also been known in which a fatty acid ester is produced from an oil or fat and an alcohol with addition of a catalyst under pressure [Ullmann Enzyclopaedie der Technischen Chemie, Vielte Edition, Vol. 11 (1976), p. 432]. That is, the reaction is carried out with an alkali catalyst or a zinc catalyst under conditions of 10 MPa, 240° C. and 7 to 8 times excess of methanol.

A technology has also been known in which fatty acid esters are produced by continuously reacting an oil or fat with an alcohol at 240° C. and 9 MPa (90 bar) in the presence of an alkali catalyst [Journal of the American Oil Chemists' Society, Vol. 61, No. 2(1984)]. Detail of the alkali catalyst, however, is unclear.

Furthermore, a process has been proposed in which the reaction is carried out using sodium carbonate or sodium hydrogen carbonate as a heterogeneous solid catalyst under conditions including the ordinary pressure or a pressure approximately the ordinary pressure at a boiling point of the used alcohol or a temperature approximately such point (JP-A-61-254255). The reaction in this process, however, is slow and thus the productivity is insufficient.

A technology has also been known in which fatty acid esters are produced by reacting an oil or fat with an alcohol within a range of 170 to 250° C. at 10 MPa (100 bar) or below in the presence of a catalyst of ZnO or a complex oxide of Zn and Al (U.S. Pat. No. 5,908,946), but the reaction is also slow.

Moreover, a process has been proposed in which a monoglyceride is selectively produced by reacting an oil or fat with an alcohol within a range of 25 to 260° C. at a pressure of 0.1 MPa (1 atm) to 10.1 MPa (100 atm) using a solid catalyst containing an alkaline earth metal oxide or the like, but there is no disclosure for a process for producing fatty acid alkyl esters and glycerol.

An object of the present invention is to provide a process for producing a fatty acid ester and glycerol from an oil or fat with an alcohol under more adequate conditions and efficiently and with a high yield, as well as a fuel and others containing the fatty acid ester.

SUMMARY OF THE INVENTION

As the result of extensive studies on a process for producing a fatty acid ester and glycerol by reacting an oil or fat with an alcohol and on a fuel containing said fatty acid ester, the present inventors have found the fact that the reaction proceeds with a high yield when the reaction is carried out with addition of a solid base catalyst and under conditions in which the oil or fat and/or the alcohol are/is in a supercritical state exceeding 260° C., or when the reaction is carried out with addition of a nickel-containing solid catalyst and under conditions in which the oil or fat and/or the alcohol are/is in a supercritical state, and thus have completed the invention. Therefore, the present invention includes the following features:

[1] A process for producing a fatty acid ester from an oil or fat and an alcohol, wherein the process comprises reacting an oil or fat with an alcohol in the presence of a solid base catalyst under conditions in which at least one of the oil or fat and the alcohol is in a supercritical state at a temperature exceeding 260° C.

[2] A process for producing a fatty acid ester from an oil or fat and an alcohol, wherein the process comprises reacting an oil or fat with an alcohol in the presence of a nickel-containing solid catalyst under conditions in which at least one of the oil or fat and the alcohol is in a supercritical state.

[3] A fuel comprising a fatty acid ester obtained by the process according to the above described [1] or [2].

[4] A fuel for diesel engine comprising a fatty acid ester obtained by the process according to the above described [1] or [2].

[5] A base oil for lubricant oil comprising a fatty acid ester obtained by the process according to the above described [1] or [2].

[6] A fuel oil additive comprising a fatty acid ester obtained by the process according to the above described [1] or [2].

DETAILED DESCRIPTION OF THE INVENTION

The reaction in the invention is described below in detail.

A principal reaction in the process of the invention is represented by the following reaction scheme (2):

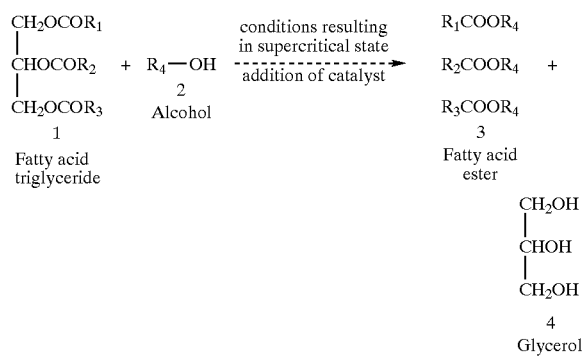

(2)

wherein $R_1$, $R_2$ and $R_3$, independent with each other, represent carbon chains of fatty acids, with carbon numbers in $R_1$, $R_2$ and $R_3$ depending on kind of the oil or fat, and $R_4$ represents a hydrocarbyl group which may be substituted with a hydrocarbyloxy group.

The oil or fat used in the present invention contains a triglyceride, an ester of a fatty acid and glycerol, as a principal component. The expression "contains a triglyceride as a principal component" refers to the fact that it contains a triglyceride in an amount of 50% by weight or more of the oil or fat.

The oil or fat used in the present invention is a material containing a triglyceride of a fatty acid shown in the reaction scheme (2) and may be a natural oil or fat or a synthetic oil or fat.

Typical examples of oil or fat include, without limitation, lard tallow, chicken tallow, butter fat, beef tallow, cocoa butter fat, corn oil, peanut oil, cotton seed oil, soybean oil, rapeseed oil, coconut butter, olive oil, safflower oil, coconut oil, oak oil, almond oil, apricot kernel oil, beef bone fat, walnut oil, castor oil, chaulmoogra oil, Chinese vegetable tallow, cod liver oil, cotton seed stearin, sesame oil, deer tallow, dolphin tallow, sardine oil, mackerel oil, horse fat, pork tallow, bone oil, linseed oil, mutton tallow, neat 's foot oil, palm oil, palm kernel oil, porpoise oil, shark oil, sperm whale oil, tung oil, whale oil and so on. In addition, the oil or fat may be a mixture of plurality of these oils or fats, an oil or fat containing a diglyceride or a monoglyceride, or a partly denatured oil or fat such as oxidized, reduced or others. Furthermore, it may be an unpurified oil or fat containing a free fatty acid, water or other, or waste oil or fat discarded by restaurant, food industries or common homes. It is preferred that an appropriate pre-treatment is applied as required.

For example, when the present invention is applied to a waste oil such as waste edible oil, it is preferred to remove insoluble solids from the oil or fat by a mesh, filter or the like before It is fed to a preheating machine, because sometimes steady operation is inhibited due to occlusion of a pressure pump or a pressure-adjusting valve by an insoluble solid if contained in the oil or fat.

The oil or fat may contain any other component than oil or fat itself. Specific examples include, without limitation, crude oil, heavy oil, light oil, mineral oil, essential oil, coal, fatty acids, saccharides, metal powders, metal salts, proteins, amino acids, hydrocarbons, cholesterol, flavors, pigment compounds, enzymes, perfumes, alcohols, fibers, resins, rubbers, paints, cements, detergents, aromatic compounds, aliphatic compounds, soot, glass, earth and sand, nitrogen-containing compounds, sulfur-containing compounds, phosphor-containing compounds, halogen-containing compounds and the like.

When the above-described substances contained in the oil or fat have a possibility of participating in the reaction, for example, have a possibility of inhibiting the reaction, or they are solid and have a possibility of occluding in the process of production or other similar possibility, it is preferred to remove them by a treatment such as filtration, distillation or the like before the reaction.

The method for distillation include, without limitation, distillation under reduced pressure, steam distillation, molecular distillation, extractive distillation and the like.

In the present invention, waste oils or fats and waste edible oils or fats can also be used as the oil or fat.

The alcohol (compound 2 in the reaction scheme (2)) used in the present invention is not particularly limited and preferably an alcohol represented by the general formula:

(1)

wherein R represents a hydrocarbyl group having 1 to 10 carbon atoms or a hydrocarbyl group having 2 to 10 carbon atoms in total substituted with a hydrocarbyloxy group.

The hydrocarbyl group having 1 to 10 carbon atoms as R includes, for example, alkyl group, aralkyl group, alkenyl group, alkynyl group and the like.

Examples of the alcohol having an alkyl group as R include methanol, ethanol, n-propanol, isopropanol, n-butanol, isobutanol, t-butanol, pentanol, hexanol, cyclohexanol, heptanol and the like.

Examples of the alcohol having an aralkyl group as R include benzyl alcohol, a-phenethyl alcohol, a-phenethyl alcohol and the like, with benzyl alcohol being preferred.

Examples of the alcohol having an alkenyl group as R include allyl alcohol, 1-methyl-allyl alcohol, 2-methyl-allyl alcohol, 3-butene-1-ol, 3-butene-2-ol and the like, with allyl alcohol being preferred.

Examples of the alcohol having an alkynyl group as R include 2-propyne-1-ol, 2-butyne-1-ol, 3-butyne-1-ol, 3-butyne-2-ol and the like.

Examples of the alcohol having a hydrocarbyl group having 2 to 10 carbon atoms in total substituted with a hydrocarbyloxy group include 2-methoxyethanol, 2-methoxypropanol, 3-methoxybutanol and the like.

Among them, preferred alcohol has an alkyl group having 1 to 4 carbon atoms as R. Specifically, the alcohol is preferably methanol wherein R is a methyl group, ethanol wherein R is an ethyl group, propanol wherein R is a propyl group, isopropanol wherein R is an isopropyl group, n-butanol wherein R is a n-butyl group, isobutanol wherein R is an isobutyl group, t-butanol wherein R is a t-butyl group, more preferably methanol or ethanol and most preferably methanol. Purity of the alcohol is not particularly limited and it is preferably 95% or above, more preferably 98% or above. The alcohol may be used independently or in admixture of two or more.

When the alcohol may exist in optical isomer forms, such optical isomers are intended to be included.

It is preferred that the alcohol is fed in a weight 1 to 100 times the theoretical feeding weight calculated according to the following formula:

Theoretical feeding weight of alcohol=(feeding weight of oil or fat×saponification value of oil or fat×molecular weight of alcohol)÷56100 wherein saponification value of oil or fat refers to an amount, represented by mg, of potassium hydroxide required for complete saponification of 1 g of the oil or fat.

The number of times less than 1 is not preferred because the reaction yield decreases. The number of times more than 100 is not preferred because the apparatus may become too large.

Representative fatty acid ester 3 producible by the reaction in the scheme (2) includes, without limitation, esters of valeric acid, caproic acid, enanthoic acid, caprylic acid, pelargonic acid, capric acid, undecylic acid, lauric acid, tridecylic acid, myristic acid, pentadecylic acid, palmitic acid, heptedecylic acid, stearic acid, nonadecanoic acid, arachic acid, behenic acid, lignoceric acid, cerotic acid, heptacosanoic acid, montanic acid, melissic acid, lacceric acid, crotonic acid, isocrotonic acid, undecylenic acid, oleic acid, elaidic acid, cetoleic acid, erucic acid, brassidic acid, sorbic acid, linoleic acid, linolenic acid, arachidonic acid, propiolic acid, stearolic acid, nervonic acid, ricinoleic acid, (+)-hydnocarpic acid, (+)-chaulmoogric acid and the like. Alcoholic residue of esters depends on the alcohol used. For, example, a methyl ester is obtained when methanol is used as the alcohol, and an ethyl ester is obtained when ethanol is used as the alcohol.

Furthermore, when optical isomers exist in the fatty acid moiety, such optical isomers are also encompassed in the present invention.

In addition, in the process of the present invention, glycerol 4 is produced as a principal product other than the fatty acid ester.

Next, the catalyst used in the present invention is described.

The solid base catalyst used in the present invention is the solid having surface basicity such as a metal oxide, metal salt, supported base, complex oxide, zeolite or the like, described in Shokubai Koza, Vol. 10, Shokubai Kakuron, Ed. Shokubai Gakkai, Published by Kodansha, 1986, page 51 [Lectures on Catalysts. Vol. 10, Individual Catalysts, Ed. Catalyst Society of Japan, Published by Kodansha, 1986, page 51]. Among them, preferred catalyst is a catalyst containing at least one of sodium carbonate, calcium oxide, calcium hydroxide, calcium carbonate and magnesium oxide.

The amount of the catalyst to be used is preferably 0.001 part by weight to 6 parts by weight, more preferably 0.005 part by weight to 3 parts by weight, based on 100 parts by weight of the oil or fat.

The solid catalyst containing a nickel compound used in the present invention includes, for example, solid catalysts containing nickel oxides (NiO, $Ni_2O_3$, complex oxides of NiO and $Ni_2O_3$), nickel carbonate, nickel hydroxide, basic nickel carbonate and the like, and further, solid catalysts on a support such as silica gel, zeolite or the like treated for impregnation of a nickel compound and others. Preferred catalysts are catalysts containing an oxide of nickel.

The amount of the catalyst containing a nickel compound to be used is preferably 0.01 part by weight to 6 parts by weight, more preferably 0.1 part by weight to 3 parts by weight, based on 100 parts by weight of the oil or fat.

The supercritical state referred to in the present invention means the following state.

Substances may exist in one of three intrinsic states, gas, liquid and solid, and in addition, may exist in fluid phase which does not condense under pressure when they are at a temperature above the critical temperature. This last state is referred to as the supercritical state.

Fluids in the supercritical state show a behavior different from the normal states of liquid or gas. The fluids in the supercritical state is a "non-liquid solvent" having a density approximate to that of liquid, a viscosity approximate to that of gas, and a thermal conductivity and a diffusion coefficient which are intervenient between those of gas and of liquid. Its low viscosity and high diffusion favor mass transfer therein, and its high thermal conductivity enables high thermal transmission. Because of such a special state, the reactivity in the supercritical state is higher than that in the normal gaseous or liquid state and thus the transesterification is promoted.

When a nickel-containing solid catalyst is used in the present invention, it is preferred to carry out the reaction under conditions in which the oil or fat and/or the alcohol are/is in a supercritical state. Such conditions include the conditions (a) to (c) indicated below:

(a) Conditions under which the mixture of the oil or fat and the alcohol is in a supercritical state.

(b) Conditions under which the alcohol is in a supercritical state.

(c) Conditions under which the oil or fat is in a supercritical state.

Among them, the conditions (a) or (b) are preferred for carrying out the reaction.

Specifically, for the condition (b) using methanol as the alcohol, the reaction is carried out at a temperature of 240° C. or more because the critical temperature of methanol is 240° C. When ethanol is used, the reaction is carried out at a temperature of 243° C. or more because the critical temperature of ethanol is 243° C. In the case of propanol, the reaction is carried out at a temperature of 264° C. or more because the critical temperature of propanol is 264° C. When butanol is used, the reaction is carried out at a temperature of 287° C. or more because the critical temperature of butanol is 287° C. When isopropanol is used, the reaction is carried out at a temperature of 236° C. or more because the critical temperature of isopropanol is 236° C. When isobutanol is used, the reaction is carried out at a temperature of 275° C. or more because the critical temperature of isobutanol is 275° C. When t-butanol is used, the reaction is carried out at a temperature of 233° C. or more because the critical temperature of t-butanol is 233° C.

When the solid base catalyst is used in the invention, the temperature at which an oil or fat is reacted with an alcohol is preferably within a range of a temperature exceeding 260° C. up to 420° C. When the reaction temperature is 260° C. or below, the reaction velocity is slow. A temperature exceeding 420° C. is not preferred because decomposition reaction or others may occur. More preferred range of temperature is a temperature exceeding 260° C. to 400° C., further preferred range of temperature is a temperature from 271° C. or more to 400° C., further more preferred range of temperature is a temperature from 280° C. or more to 400° C.

When a nickel-containing solid catalyst is used in the invention, the temperature at which an oil or fat is reacted with an alcohol is within a range of a temperature at which the oil or fat and/or the alcohol are/is in a supercritical state. The upper limit of the reaction temperature is not critical but preferably 400° C. or below, because of possible decomposition reaction.

The density condition of the alcohol in a reaction vessel in which the oil or fat is reacted with the alcohol according to the present invention is preferably within a range of 0.01 $g/cm^3$ to 0.4 $g/cm^3$, and the pressure condition is preferably within a range of 0.5 MPa to 25 MPa.

The time period for reacting an oil or fat with an alcohol according to the present invention is preferably within a range of 0.1 minute to 180 minutes, more preferably within a range of 0.5 minute to 120 minutes, and further, most preferably within a range of 1 minute to 60 minutes.

The reaction can be carried out in various reaction modes. For example, the reaction may be carried out either in batch system or in flow system.

In addition, in the invention, the oil or fat and the alcohol may either be homogeneously mixed throughout the reaction or be separated into two phases insofar as the reaction can occur.

When they are separated into two phases, the reaction can be promoted more effectively by enlarging the contact surface between the two phases, for example, through agitation of the reaction system.

The reaction mixture after the reaction contains a fatty acid ester, glycerol and an excess unreacted alcohol, and in addition, may contain unreacted raw materials and other impurities.

The fatty acid ester is purified from the reaction mixture to a purity required for the individual application. Methods for purification are not particularly limited and general methods such as distillation, extraction and the like can be applied depending on the property of the fatty acid ester to be produced.

When a case wherein methanol is used as the alcohol is taken as an example, the mixture is stood for separation of light liquid and heavy liquid after recovering an excess (or unreacted)methanol component by evaporation. Separation of the solid base catalyst and the nickel-containing solid catalyst used in the present invention from a reaction solution is rather easy and thus after-treatment of the reaction solution is rather simple an compared with the case of sodium hydroxide or the like. The light liquid contains fatty acid methyl ester as a principal component and can be utilized as a raw material for fuel for diesel engines or a raw material for natural higher alcohol. The heavy liquid containing glycerol as a principal component can be utilized as a raw material for industrial glycerol.

Representative means for separation of unreacted alcohol includes, without limitation, mixer-settler extraction, liquid-liquid extraction, extraction with a pulse column, jet extraction, Podbielniak rotary extraction and the like, in addition to distillation such as distillation under reduced pressure. The fatty acid ester maybe taken out after completely separating the alcohol or may be recovered in a state containing a residual alcohol.

Depending on structure of the oil or fat as the raw material, the fatty acid ester produced according to the present invention is generally in the form of a mixture of several fatty acid esters when a natural oil or fat is used. In this case, depending on the application, either the mixture itself can be used or a specific fatty acid ester can be used after isolating it by a common method such as distillation, extraction or the like, as required.

The fatty acid ester produced by the above-described manner can be used in fuels such as a fuel for diesel engine, a base oil for lubricant oil, an additive for fuel oil and the like by itself or in admixture with other components according to the requirements derived from the use.

As described in SHINPEN JIDOUSHA KOGAKU HANNDOBUKKU (Ed. SHADANNHOUJINN JIDOUSHAGIJUTSUKAI) [A New Handbook of Automobile Engineering (Ed. Corporation of Automobile Technology)], ignitability and viscosity are important items in the case of use in the fuel for diesel engine. Because use of a fatty acid ester having a relatively low viscosity may be a cause for abrasion or seizing, it is essential to use a fatty acid ester having a viscosity adapted to diesel engine. In addition, because a fatty acid ester with too high molecular weight may be a cause for odor or smoke, such ester is not preferred.

Examples of preferably used esters for use in fuel for diesel engine include fatty acid methyl ester, fatty acid ethyl ester, fatty acid isopropyl ester, fatty acid isobutyl ester and the like. Among them,fatty acid isopropyl ester and fatty acid isobutyl ester produce a fuel for diesel engine having a high performance at a low temperature.

The viscosity is also an important item in the Case of use in base oil for lubricant oil. While it is desirable that the ester for summer season has a relatively high viscosity in order to obtain a high lubricity, a fatty acid ester with relatively low viscosity and high flowability is desirable when it is used in the winter season or in a place of low temperature. Therefore, a wide variety of fatty acid esters can be used as a base oil for lubricant oil.

In the case of the additive for fuel oil, the fatty acid ester is added to a fuel mainly for decreasing friction. The ester has a role similar to that in the lubricant oil and similar properties to those in the base oil for lubricant oil are preferred.

Depending on use, the fatty acid esters as produced may contain glycerol, excess unreacted alcohol, unreacted oil or fat and other impurities, in a reaction mixture after reaction is completed, if they have no problem in use.

In addition, the yield can be increased by repeating the reaction under conditions provided in the present invention or other means, when required by desired use.

According to the present invention, a process for producing a fatty acid ester from an oil or fat and an alcohol by a simple convenient process and with a high yield, as well as a fuel and others containing a fatty acid ester, can be provided. Therefore, the invention has a great industrial value. In addition, the invention is useful from the viewpoint of reuse of resources and prevention of public pollution.

EXAMPLES

The present invention will now be described in more detail with reference to Examples, which should not be construed as a limitation upon the scope of the invention.

Example 1

After weighing 0.860 g of soybean oil as the oil or fat containing triglycerides as principal components, 1.240 g of methanol as the alcohol, and 5.8 mg of powdery anhydrous sodium carbonate as the catalyst, they were charged in a stainless steel reaction tube (about 4.5 cm$^3$), which was then sealed. The reaction tube was placed in a fluidized bed sand bath controlled at a temperature of 300° C. and the reactants were heated and reacted. After 10 minutes, the tube was taken out (placed for 10 minutes in the sand bath) and immediately placed in water for cooling.

The amount of methanol used in this reaction was about 13 times the theoretical amount necessary for complete methyl-esterification of the soybean oil. The temperature at a wall of the reaction tube was measured by attaching thermocouple. The wall exceeded about 260° C. after 2 minutes and was about 300° C. after 10 minutes. The density of methanol at the initial state of the reaction was 0.28 g/cm$^3$, as calculated from a reaction volume.

Then, the reaction solution in the reaction tube was subjected to the first recovery and repeatedly washed three times with methanol. The used catalyst was separated by precipitation in the recovered solution. The reactivity was evaluated by quantitatively analyzing the methyl ester component and the glycerol component in the recovered solution using gas chromatography (GC). It was found that the yield of the fatty acid methyl ester was about 99% and that of glycerol was about 99% (as shown in Table 1). The yields here were values calculated on the basis of a reaction in which 3 moles of fatty acid methyl easters and 1 mole of glycerol were formed from 1 mole of soybean oil.

The components in the reaction solution were analyzed by size exclusion chromatography (SEC) in which compounds were separated according to differences in molecular weight. The results are also shown in Table 1.

Examples 2, 3 and 4

Tests in Example 1 were substantially repeated except that calcium oxide, calcium hydroxide and magnesium oxide, respectively, were used as the catalyst. The results of analysis by GC and SEC on the recovered solutions are shown in Table 1.

Example 5

Tests in Example 1 were substantially repeated except that the temperature in the fluidized bed sand bath was controlled to 350° C. and the reaction tube was placed for 4 minutes. The temperature at the wall of the reaction tube exceeded 260° C. after about 1.3 minute and was about 340° C. after 4 minutes. The results of analysis by GC and SEC on the recovered reaction solution are shown in Table 1.

Examples 6, 7 and 8

Tests in Example 1 were substantially repeated except that calcium hydroxide, calcium oxide and calcium carbonate, respectively, were used as the catalyst and soybean oil in which 0.01% of powders of catalysts were previously added and dispersed was used. The results of analysis by GC and SEC on the recovered reaction solutions are shown in Table 1.

Example 9

Tests in Example 1 were substantially repeated except that 0.744 g of a soybean oil as the oil or fat in which 0.01% of powders of sodium calcium catalyst was previously added and dispersed and 1.084 g of methanol as the alcohol were used, the temperature in the sand bath was controlled to 400° C. and the reaction tube was placed for 2 minutes. The temperature at the wall of the reaction tube in this test exceeded about 260° C. after 0.6 minute and was about 360° C. after 2 minutes.

The results of analysis by SEC on the recovered reaction solution are shown in Table 1.

Comparative Example 1

Tests in Example 1 were substantially repeated except that the temperature in the fluidized bed sand bath was controlled to 250° C. and the reaction tube was placed for 10 minutes. The temperature at the wall of the reaction tube was about 230° C. after 2 minutes and was about 250° C. after 10 minutes. The results of analysis by GC and SEC on the recovered reaction solution are shown in Table 1.

Example 10

After weighing 0.861 g of soybean oil as the oil or fat containing triglycerides as principal components, 1.242 g of methanol as the alcohol, and 10.9 mg of powdery nickel oxide (complex oxide of NiO and $Ni_2O_3$) as the catalyst, they were charged in a stainless steel reaction tube (about 4.5 $cm^3$), which was then sealed. The reaction tube was placed in a fluidized bed sand bath controlled at a temperature of 300° C. and the reactants were heated and reacted, After 10 minutes, the tube was taken out and immediately placed in water for cooling. The amount of methanol used in this reaction was about 13 times the theoretical amount necessary for complete methyl-esterification of the soybean oil. The temperature at a wall of the reaction tube was measured by attaching thermocouple. The wall exceeded about 260° C. after 2 minutes indicating that the temperature exceeded the critical temperature of methanol. The density of methanol at the initial state of the reaction was 0.28 $g/cm^3$, as calculated from a reaction volume.

Then, the reaction solution in the reaction tube was subjected to the first recovery and repeatedly washed three times with methanol. The used catalyst was separated by precipitation in the recovered solution. The reactivity was evaluated by quantitatively analyzing the methyl ester component and the glycerol component in the recovered solution using gas chromatography. It was found that the yield of the methyl ester was about 98% and that of glycerol was about 91%. The yields here were values calculated on the basis of a reaction in which 3 moles of fatty acid methyl esters and 1 mole of glycerol were formed from 1 mole of soybean oil.

Example 11

Tests in Example 10 were substantially repeated except that 0.867 g of a soybean oil, 1.241 g of methanol and 29.1 mg of the powdery nickel oxide were used. The results of analysis made on the recovered reaction solution showed that the yield of the methyl ester was about 98% and that of glycerol was about 91%.

Comparative Example 2

Tests in Example 10 were substantially repeated except that 0.858 g of a soybean oil, 1.239 g of methanol and 10.2 mg of powdery zinc oxide (ZnO) were used. The results of analysis made on the recovered reaction solution showed that the yield of the methyl ester was about 58% and that of glycerol was about 30%.

TABLE 1

| | Soybean oil (g) | Methanol (g) | Catalyst compound | Amount of catalyst (mg) | Temperature (° C.) | Period (min.) | Yield (%) of MES | Yield (%) of glycerol | Analysis by GPC | | | |
|---|---|---|---|---|---|---|---|---|---|---|---|---|
| | | | | | | | | | MES % | MG % | DC % | TG % |
| Example 1 | 0.860 | 1.240 | Sodium carbonate | 5.8 | 300 | 10 | 99% | 99% | 98% | 2% | 0% | 0% |
| Example 2 | 0.854 | 1.241 | Calcium oxide | 5.0 | 300 | 10 | 97% | 82% | 98% | 2% | 0% | 0% |
| Example 3 | 0.864 | 1.249 | Calcium hydroxide | 5.9 | 300 | 10 | 98% | 87% | 99% | 1% | 0% | 0% |

TABLE 1-continued

| | Soybean oil (g) | Methanol (g) | Catalyst compound | Amount of catalyst (mg) | Temperature (° C.) | Period (min.) | Yield (%) of MES | Yield (%) of glycerol | Analysis by GPC | | | |
|---|---|---|---|---|---|---|---|---|---|---|---|---|
| | | | | | | | | | MES % | MG % | DC % | TG % |
| Example 4 | 0.853 | 1.239 | Magnesium oxide | 11.2 | 300 | 10 | 91% | 73% | 86% | 7% | 4% | 3% |
| Example 5 | 0.861 | 1.243 | Sodium carbonate | 10.5 | 350 | 4 | 95% | 90% | 99% | 1% | 0% | 0% |
| Example 6 | 0.845 | 1.223 | Calcium hydroxide | 0.085 | 300 | 10 | 98% | 103% | 96% | 3% | 2% | 0% |
| Example 7 | 0.842 | 1.228 | Calcium oxide | 0.084 | 300 | 10 | 97% | 104% | 96% | 3% | 1% | 0% |
| Example 8 | 0.852 | 1.223 | Calcium carbonate | 0.085 | 300 | 10 | 98% | 103% | 96% | 3% | 1% | 0% |
| Example 9 | 0.744 | 1.084 | Calcium hydroxide | 0.074 | 400 | 2 | — | — | 95% | 3% | 2% | 0% |
| Comparative example 1 | 0.866 | 1.248 | Sodium carbonate | 10.0 | 250 | 10 | 87% | 68% | 78% | 6% | 6% | 10% |

In Table, MES means methyl ester, MG monoglyceride, DG diglyceride and TG triglyceride.

What is claimed is:

1. A process for producing a fatty acid ester from an oil or fat and an alcohol, wherein the process comprises reacting an oil or fat with an alcohol in the presence of a solid base catalyst comprising at least one component selected from the group consisting of sodium carbonate, calcium oxide, calcium hydroxide, calcium carbonate and magnesium oxide under conditions in which at least one of the oil or fat in an amount of 0.001 parts by weight or more based on 100 parts by weight of the oil or fat and the alcohol is in a supercritical state at a temperature of 270° C. or more, said solid base catalyst being present in an amount of 3 to 6 parts by weight based on 100 parts by weight of the oil or fat.

2. A process for producing a fatty acid ester from an oil or fat and an alcohol, wherein the process comprises reacting an oil or fat with an alcohol in the presence of a nickel-containing solid catalyst under conditions in which at least one of the oil or fat and the alcohol is in a supercritical state.

3. The process according to claim 2, wherein the nickel-containing solid catalyst is a catalyst containing an oxide of nickel.

4. The process according to claim 1 or 2, wherein the alcohol is in a supercritical state.

5. The process according to claim 4, wherein the alcohol is represented by the following formula (1):

$$R\text{—}OH \quad (1)$$

wherein R is a hydrocarbyl group having 1 to 10 carbon atoms, or a hydrocarbyl group substituted by a hydrocarbyloxyl group which substituted hydrocarbyl group has 2 to 10 carbon atoms.

6. The process according to claim 5, wherein R in the formula (1) is an alkyl group having 1 to 4 carbon atoms.

7. The process according to claim 5, wherein R in the formula (1) is methyl group or ethyl group.

8. The process according to claim 5, wherein R in the formula (1) is methyl group.

9. The process according to claim 1 or 2, wherein the oil or fat is a waste oil or fat.

10. The process according to claim 1 or 2, wherein the oil or fat is a waste edible oil.

11. The process according to claim 1, wherein the alcohol is in a supercritical state at a temperature within the range of from 270 to 400° C.

* * * * *